United States Patent
Ma et al.

(10) Patent No.: US 8,765,925 B2
(45) Date of Patent: Jul. 1, 2014

(54) PROCESS FOR PREPARATION OF TIMOSAPONIN B II

(75) Inventors: Baiping Ma, Beijing (CN); Hao Chen, Beijing (CN); Chengqi Xiong, Beijing (CN); Liping Kang, Beijing (CN); Jie Zhang, Beijing (CN)

(73) Assignee: Institute of Radiation Medicine, Academy of Military Medical Sciences, PLA, Beijing (CN)

( * ) Notice: Subject to any disclaimer, the term of this patent is extended or adjusted under 35 U.S.C. 154(b) by 1378 days.

(21) Appl. No.: 11/579,101

(22) PCT Filed: Apr. 21, 2005

(86) PCT No.: PCT/CN2005/000554
§ 371 (c)(1),
(2), (4) Date: Nov. 27, 2006

(87) PCT Pub. No.: WO2005/105824
PCT Pub. Date: Nov. 10, 2005

(65) Prior Publication Data
US 2009/0012277 A1    Jan. 8, 2009

(30) Foreign Application Priority Data

Apr. 29, 2004  (CN) .......................... 2004 1 0037346
Mar. 25, 2005  (CN) .......................... 2005 1 0059467

(51) Int. Cl.
*C07H 1/08*   (2006.01)
*C07H 19/01*  (2006.01)
*C07J 71/00*  (2006.01)

(52) U.S. Cl.
USPC .............................. 536/6.3; 536/6.1; 536/128

(58) Field of Classification Search
USPC ............................................ 536/6.3, 6.1, 128
See application file for complete search history.

(56) References Cited

U.S. PATENT DOCUMENTS 6,495,140 B1 * 12/2002 Collins et al. ................. 424/745

FOREIGN PATENT DOCUMENTS

JP    04-54194 A      2/1992
JP    2000-204043     7/2000

OTHER PUBLICATIONS

Scott, R.P.W. Techniques and Practice of Chromatography, 1995, Marcel Dekker, Inc., v. 70, p. 303-307 and 321-324.*
Search for definition of diacolation, Merriam-Webster Online, http://www.merriam-webster.com/dictionary/diacolation, accessed online on Jul. 6, 2009.*
Search for definition of diacolation, Dictionary.com, http://dictionary.reference.com/browse/diacolation, accessed online on Jul. 8, 2009.*
Nagumo et al. Yakugaku Zasshi, 1991, 111(6), p. 306-310.*
Dinan et al. J. Chromatogr., A, 2001, 935, p. 105-123.*
Oleszek, W.A. J. Chromatogr., A, 2002, 967, p. 147-162.*
International Search Report and International Preliminary Report on Patentability (Chapter 1) for PCT/CN/000554, dated Aug. 4, 2005.
Ma, Baiping, et al., "Studies on the Furostanol Saponins from *Anemarrhena asphodeloides* Bunge," Yaoxue Xuebao, vol. 31, No. 4, 1996, p. 271-277, the whole document.
Zhang, Jianying, et al., "Effect of six steroidal saponins isolated from *Anemarrhenae* rhizoma on platelet aggregation and hemolysis in human blood," Clinica Chimica Acta, vol. 289, No. 1-2, 1999, pp. 79-88, the whole document.
Nakashima, Noboru, et al., "Isolation of Pseudoprototimosaponin AIII from Rhizomes of *Anemarrhena asphodeloides* and its Hypoglycemic Activity in Streptozotocin-Induced Diabetic Mice," Journal of Natural Products, vol. 56, No. 3, Mar. 1993, pp. 345-350, the whole document.

* cited by examiner

*Primary Examiner* — Shaojia Anna Jiang
*Assistant Examiner* — Jonathan S Lau
(74) *Attorney, Agent, or Firm* — Harness, Dickey & Pierce, P.L.C.

(57) ABSTRACT

A method for preparation of Timosaponin BII, which uses Chinese traditional medicine Rhizoma Anemarrhenae or fresh rhizoma or fibrous root of *Anemarrhena asphodeloides* Bge. as raw material, and comprises isolation of Timosaponin BII by one or more processes selected from solvent extraction, resin adsorption, polyamide chromatography, reversed phase column chromatography, Sephadex LH-20 column chromatography, etc, combining with conventional drying method such as reduced pressure drying, freeze drying, spray drying, and so on. Timosaponin BII obtained by the present method is of over 90% purity, and the method is simple, practicable and suitable for industrial production.

10 Claims, No Drawings

PROCESS FOR PREPARATION OF TIMOSAPONIN B II

FIELD OF THE INVENTION

The invention relates to a process for preparation of Timosaponin BII.

BACKGROUND

Chinese traditional medicine Rhizoma Anemarrhenae is the rhizoma of the *Anemarrhena asphodeloides* Bge, (Liliaceae), widely distributed in Hebei, Neimenggu, Shanxi province, northeast of China and some other areas. Due to the heat-clearing and fire-purging function and the action of promoting the production of body fluid and nourishing the lung, it was frequently used in Traditional Chinese Medicine clinic. The main components of *Anemarrhena asphodeloides* Bge. are steroidal saponins, together with flavones, oligosaccharides, polysaccharides and fatty acids, et, al. Pharmacological studies show that it has antibiosis, antiviral, pyretolysis, antidiabetic, conscious-sedation, inhibition of platelet aggregation, anticancer and radioprotective effects, etc.

Timosaponin BII, also named Prototimosaponin AIII, is the main component of rhizoma of *Anemarrhena asphodeloides* Bge. It has the structure of (25S)-26-O-β-D-glucopyranosyl-22-hydroxy-5β-furostane-3β, 26-diol-3-O-β-D-glucopyranosyl-(1→2)-β-D-galactopyranoside. It has the following formula:

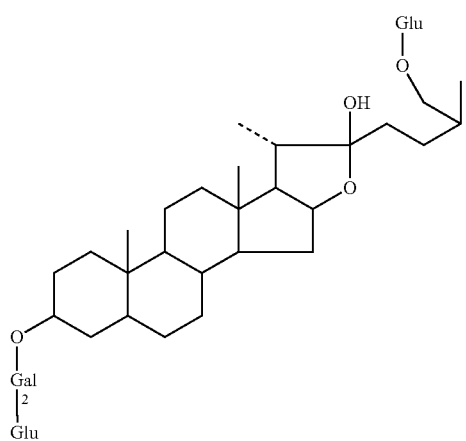

Timosaponin BII was first isolated by Toshio KAWAZAKI in 1963, but he didn't give its structure. In 1991, Seiji NAGUMO first elucidated the structure of Timosaponin BII (Seiji NAGUMO et al, YAKUGAKU ZASSHI, 1991; 111 (1) 306-310). After that Noboru Nakashima (NOBORU NAKASHIMA et al, Journal of Natural Products, 1993; 56(3):345-350), Bai-ping Ma (Bai-ping Ma et al, Acta. Pharm. Sin. 1996; 31 (4): 271-277), Masayasu Kimula (Masayasu KIMURA et al, Biol. Pharm. Bull, 1996; 19 (7): 926-931) and Jian-ying Zhang (Jian-ying ZHANG et al, Clinica Chimica Acta, 1999; 289: 79-88) reported the isolation and activity of Timosaponin BII. Researches indicated that Timosaponin BII has the activities of antidiabetic, inhibition of platelet aggregation, scavenging of free radical and anti-dementia. In almost all the prior art references, the Timosaponin BII was prepared by n-butanol extraction, normal phase silica gel column chromatography, macroporous resin column chromatography and HPLC. But it is ease to emulsify in n-butanol extraction, the amount of sample is limited on silica gel column chromatography, it is difficult to reproduce silica gel, it is difficult to recover the eluent of chloroform-methanol-water. Therefore, the reported methods usually had a difficult process, low yield, low purity and not amenable to industrialized preparation. Even using macroporous resin and reversed-phase liquid chromatography, the eluent of methanol-water will result in the C-22 hydroxyl methoxylation of Timosaponin BII to form a certain fraction of Timosaponin BI (Seiji NAGUMO et al., YAKUGAKU ZASSHI, 1991; 111 (1): 306-310). So these methods would waste some samples and could only generate the mixture of Timosaponin BII and Timosaponin BI, and it is too difficult to get the pure Timosaponin BII.

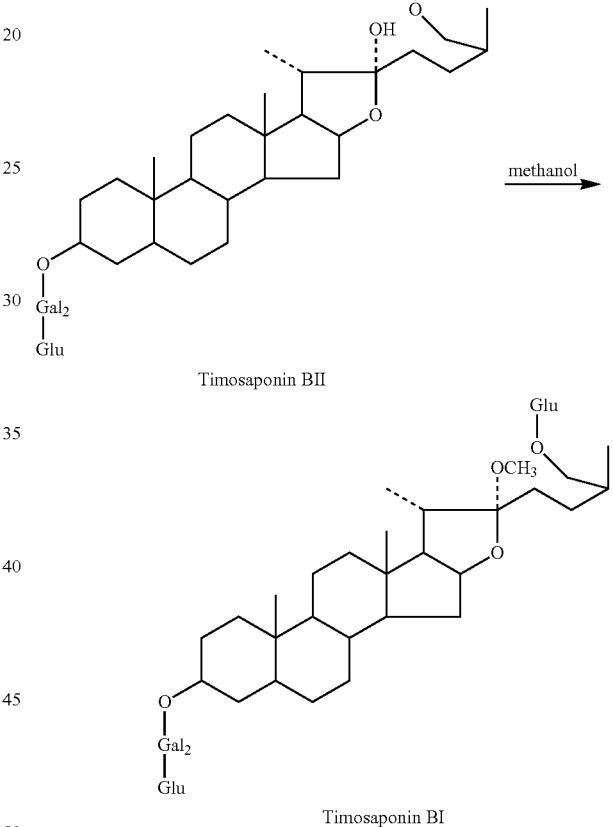

For these reasons, it is necessary to improve the preparative method of Timosaponin BII.

BRIEF DESCRIPTION OF THE INVENTION

An object of the invention is to provide an improved preparation method of Timosaponin BII. The method avoids using n-butanol and silica gel column chromatography in the extraction and purification, avoids using methanol in the elution, and thereby ensures the high purity and yield of Timosaponin BII.

Accordingly, this invention relates to an improved method for preparing Timosaponin BII, comprising:

a) providing as raw material the decoction pieces of Chinese traditional medicine Rhizoma Anemarrhenae or fresh rhizome or root of *Anemarrhena asphodeloides* Bge and extracting with a solvent selected from the group consisting of water, acetone, ethanol, propanol, and the mixture of at least two of them;

b) separating the extract from a) by one or more methods selected from the group consisting of resin adsorption, polyamide chromatography, reversed-phase column chromatography and Sephadex LH-20 column chromatography, and eluting with an eluent selected from the group consisting of water, acetone, acetonitrile, ethanol, propanol and a mixture of at least two of them;

c) combining the eluents of b), drying and obtaining Timosaponin BII.

According to the present invention, in the step a), the solvent used may be any one of water, acetone, ethanol and propanol, or a mixture consisting of two or more of them in any proportion. The extract may be immersion extraction or ultrasonic extraction in ultrasonic extractor at room temperature, or immersion extraction or reflux extraction under conditions of heating, and the extraction may be conducted one or more times. In the step a), the preferred extraction methods are as follows:

decoction with water; or reflux, percolation or ultrasonic extraction with 10 to 90% ethanol solution in water; or reflux, percolation or ultrasonic extraction with 10 to 80% acetone solution in water.

According to the present invention, in the step b), concerning the resin adsorption, the resins used may be D-101 type adsorptive resins, AB-8 type adsorptive resins, XAD-2 type adsorptive resins, HP20 type adsorptive resins, SP825 type adsorptive resins, SP700 type adsorptive resins, CHP-20P type adsorptive resins or SP70 type adsorptive resins, or others types of polystyrene (PS) macroporous adsorptive resins. The eluent used may be one or more of water, acetone, ethanol, and propanol. The eluting method may be isocratic elution or gradient elution.

In a specific embodiment, the centrifugation supernatant or filtrate of the extract is adsorbed on a macroporous resin, and the impurity may be removed by eluted with water or low concentration of acetone or lower alcohol (e.g., ethanol or propanol) in water, wherein the concentration may be 5 to 30% and the volume may be 2 to 7 times column volume (2 to 7 BV). Then the column is eluted with a higher concentration of acetone or lower alcohol (e.g., ethanol or propanol) in water, wherein the concentration may be 20 to 70% and the volume may be 2 to 7 times column volume (2 to 7 BV). Depending on the detection results all or a part of the eluate is collected, the solvent is recovered and the residue is concentrated to give the raw Timosaponin BII.

According to the present invention, as an alternative method that may be used in step b), the polyamide chromatography may be a column chromatography or static adsorption filtration method, and the eluent may be one or more of water, acetone, acetonitrile, ethanol and propanol. Eluting method may be isocratic elution or gradient elution.

In a specific embodiment, the aqueous solution of Timosaponin BII is loaded on the polyamide column and eluted with water or low concentration of acetone or lower alcohol (e.g., ethanol or propanol) in water, wherein the concentration may be 0 to 15% and the volume may be 2 to 5 times column volume (2 to 5 BV). Depending on the detection results, all or a part of the eluate is collected, the solvent is recovered and the residue is concentrated to give the Timosaponin BII. Alternatively, the polyamide is added to the aqueous solution comprising Timosaponin BII, agitated sufficiently, stood, filtered by Buchner's filter, and eluted with water or low concentration of acetone or lower alcohol in water. Depending on the detection results, all or a part of the eluate is combined, the solvent is recovered and the residue is concentrated to give the Timosaponin BII. The polyamide may be regenerated with high concentration of acetone, ethanol or propanol in water or with acid or alkali.

As an alternative method that may be used in step b) of the method according to the present invention, the reversed-phase column chromatography may be normal pressure or pressurized reversed-phase column chromatography. The column stuffing may be Silica gel reversed phase 18 (Silica gel RP-18) or Silica gel reversed phase 8 (Silica gel RP-8). The eluent may be one or more of acetonitrile-water, acetone-water, ethanol-water, and propanol-water. Eluting method may be isocratic elution or gradient elution.

In a specific embodiment, the sample that contains Timosaponin BII is dissolved in the eluent, the solution is chromatographed on the reverse-phase column and eluted with one or more of acetonitrile-water, acetone-water, ethanol-water, and propanol-water, wherein the concentration of organic solvent may be 15 to 60%, and the eluate is collected fractionally. Depending, on the detection results, a part of the eluate is combined, the solvent is recovered and the residue is concentrated to give the Timosaponin BII.

As an alternative method that may be used in step b) of the method according to the present invention, the Sephadex LH-20 column chromatography may be normal pressure or pressurized column chromatography. The eluent may be one or more of acetonitrile-water, acetone-water, ethanol-water, and propanol-water, and the eluting method may be isocratic elution or gradient elution.

In a specific embodiment, a sample that contains Timosaponin BII is dissolved in the eluent, chromatographed on Sephadex LH-20 and eluted with one or more of acetonitrile-water, acetone-water, C2 to C5 alcohol (e.g., ethanol and propanol)—water, wherein the concentration of organic solvent may be 5 to 60%, and the eluate is collected fractionally. Depending on the detection results, a part of the eluate is combined, the solvent is recovered and the residue is concentrated to give the Timosaponin BII.

According to the present invention, in step c) a drying method known in the art may be used, for example, drying under reduced pressure, freeze-drying or spray drying.

The invention solved the problems of complication of the prior art methods, especially the low purity and low yield of Timosaponin BII due to using the n-butanol, methanol and silica gel column chromatography. According to the method of the present invention, the purity of Timosaponin BII prepared is higher than 90%; and this method is simple, practicable and amenable to industrialization.

EXAMPLES

The following examples will illustrate the invention in detail, but are not intended to limit the invention by any means.

Example 1

Preparation of Timosaponin BII

The decoction pieces of Chinese traditional medicine Rhizoma Anemarrhenae (8 kg) were ground, to which 48 L of 50% ethanol was added. The drug was immersed for one hour and then reflux extracted for one hour before filtering. The residue was similarly reflux extracted for more two times. The ethanol extract was combined, the ethanol was recovered and the residue was concentrated under reduced pressure until 40 L. The pretreated macroporous absorptive resin SP825 (Mitsubishi Co., Japan) was loaded on the column (18 L), which was equilibrated with water. The concentrated extract was filtered, and the filtrate was chromatographed on the column and washed with water to remove the impurity. Thereafter, the column was eluted sequentially with 3 times column volume (3BV) of 35% ethanol, 3BV of 50% ethanol and 38V of 95% ethanol. The detection results showed that Timosaponin BII was mainly collected in the traction of 50% ethanol. This fraction was concentrated to remove ethanol until a small volume, and then ethanol was added to a 35% final concentration for further use. The regenerated macroporous resin SP825 column (18 L) was equilibrated with 35% ethanol. The sample above was chromatographed on the column and eluted with 6BV of 45% ethanol. The eluate was collected in fractions with 2,000 mL per fraction, and the purity of each fraction was detected by HPLC. The fractions 18 to 30 were combined and concentrated to remove ethanol until a small volume. The obtained solution was chromatographed on a pretreated polyamide column (6 L, 30-60 meshes, Linjiang Reagent Chemical Plant), and eluted with 5BV of water. The fraction containing coloring material at the beginning was abandoned, and the eluate was collected in fractions with 600 mL per fraction, and detected by HPLC. The fractions 6 to 23 were combined, concentrated, and spray dried to give Timosaponin BII (56.5 g). The yield of the product was 0.71% of the raw medicinal material, and the purity, as detected by HPLC, was 90.8%.

Example 2

Preparation of Timosaponin BII

The decoction pieces of Chinese traditional medicine Rhizoma Anemarrhenae (5 kg) were ground, to which 30 L of 30% acetone was added. The drug was immersed for two hours and then extracted for 0.5 hour with an ultrasonic wave oscillator before filtering. The residue was similarly ultrasound extracted for more two times. The acetone extract was combined, the acetone was recovered and the residue was concentrated under reduced pressure until 30 L. A pretreated macroporous resin AB-8 (Tianjin Nankai Chemical Plant) was loaded on a column (18 L), which was equilibrated with water. The concentrated extract was filtered, and the filtrate was chromatographed on the column and eluted with water to remove the impurity. Thereafter, the column was eluted in sequence with 3 times column volume (3BV) of 20% ethanol, 38V of 50% ethanol and 3BV of 95% ethanol. The detection results showed that Timosaponin BII was mainly collected in the fraction of 50% ethanol. This fraction was concentrated to remove ethanol until a small volume, and then dried in vacuo to obtain crude sample of Timosaponin BII (286 g). 80 g of the crude sample vas dissolved with 1,000 mL of 25% acetone, and loaded on a SILICA GEL RP-18 column (6.5 L), which was pre-equilibrated with 25% acetone. The column was eluted in sequence with 28% acetone (20,000 mL) and 30% acetone (20,000 mL), and then regenerated with 80% acetone (13,000 mL). The eluates of 28% acetone and 30% acetone were collected in fractions with 600 mL per fraction, and the purity of each fraction was detected by HPLC. The fractions 6 to 21 were combined and concentrated to remove acetone until a small volume and then lyophilized to obtain Timosaponin BII (12.9 g). The yield of the product was 0.92% of the raw medicinal material, and the purity, as detected by HPLC, was 94.3%.

Example 3

Preparation of Timosaponin BII

The decoction pieces of Chinese traditional medicine Rhizoma Anemarrhenae (5 kg) were ground, to which 30 L of 30% acetone was added. The drug was immersed for two hours and then extracted for 0.5 hour with an ultrasonic wave oscillator before filtering. The residue was similarly ultrasound extracted for more two times. The acetone extract was combined, the acetone was recovered and the residue was concentrated under reduced pressure until 30 L. A pretreated macroporous resin AB-8 (Tianjin Nankai Chemical Plant) was loaded on a column (18 L), which was equilibrated with water. The concentrated extract was filtered, and the filtrate was chromatographed on the column and eluted with water to remove the impurity. Thereafter, the column was eluted in sequence with 3BV of 20% ethanol, 3BV of 50% ethanol and 3BV of 95% ethanol. The detection results showed that Timosaponin BII was mainly collected in the fraction of 50% ethanol. This fraction was concentrated to remove ethanol until a small volume, and then dried in vacuo to obtain crude sample of Timosaponin BII (290 g). 80 g of the crude sample was dissolved in 1,000 mL of 25% acetone solution, and chromatographed on a SILICA GEL RP-18 column (6.5 L), which was pre-equilibrated with 32% methanol. The column was eluted in sequence with 32% methanol (20,000 mL) and 34% methanol (20,000 mL), and then regenerated with 90% methanol (15,000 mL). The eluates of 32% methanol and 34% methanol were collected in fractions with 600 mL per fraction, and the purity of each fraction was detected by HPLC. The fractions 8 to 19 were combined and concentrated to remove methanol until a small volume and then lyophilized to obtain Timosaponin BII (9.79 g). The purity, as detected by HPLC, was 73.1%. The sample was dissolved in 30% acetone, refluxed at 95° C. for 5 hours, and concentrated to remove acetone until a small volume and then lyophilized to obtain Timosaponin BII (9.7 g). The yield of the product was 0.70% of the raw medicinal material, and the purity, detected by HPLC, was 93.9%.

Example 4

Preparation of Timosaponin BII

The fresh rhizomes of *Anemarrhena asphodeloides* Bunge (4 kg) was sliced, and decocted with 10 L water for 1 hour before filtering. 8 L of water was added to the residue, and decocted for 1 hour before filtering. The filtrates were combined and concentrated under reduced pressure until 10 L, to which ethanol was added to 25% final concentration to give an extract for further use. A pretreated macroporous resin D101 (Tianjin Agrochemical Plant) was loaded on a column (6 L), which was equilibrated with 25% ethanol. The extract solution was filtered, and the filtrate was chromatographed on the column. Thereafter, the column was eluted in sequence with 38V of 25% ethanol, 3BV of 35% ethanol and 3BV of 90% ethanol. The detection results showed that Timosaponin BII was mainly collected in the fraction of 35% ethanol. This fraction was concentrated to remove ethanol until a small volume. The concentrated eluate was chromatographed on a pretreated polyamide column (6 L, 30-60 meshes, Linjiang Reagent Chemical Plant), and eluted with 5BV of water. The fraction containing coloring material at the beginning was abandoned, and the eluate was collected in fractions with 600 mL per fraction, and detected by HPLC. The fractions 8 to 24 were combined, concentrated, and spray dried to obtain crude sample of Timosaponin BII (51 g). About 40 g of the crude sample was dissolved in 200 mL of 35% ethanol, and chromatographed on a Sephadex LH-20 column (8.5 L), which was pre-equilibrated with 35% ethanol. The column was eluted with 35% ethanol (50,000 mL), and then regenerated with 95% ethanol (20,000 mL). The eluate of 35% ethanol was collected in fractions with 800 mL per fraction, and the purity of each fraction was detected by HPLC. The fractions 16 to 35 were combined, concentrated to remove ethanol until a small volume, and then lyophilized to obtain to give Timosaponin BII (11.2 g). The yield of the product was 0.36% of the fresh rhizomes (corresponding to the yield of 1.07% of the dry medicinal material), and the purity, as detected by HPLC, was 92.3%.

Example 5

Preparation of Timosaponin BII

The fibrous roots of *Anemarrhena asphodeloides* Bunge (2 kg) was cut, and decocted with 16 L water for 1 hour before filtering. 12 L of water was added to the residue, and decocted for 1 hour before filtering. The filtrates were combined and concentrated under reduced pressure until 12 L, to which acetone was added to obtain a 15% final concentration for further use. A pretreated macroporous resin SP700 (Mitsubishi Co., Japan) was loaded on a column (6 L), which was equilibrated with 15% acetone. The extract was filtered, and the filtrate was chromatographed on the column. Thereafter, the column was eluted in sequence with 3BV of 25% acetone, 3BV of 35% acetone and 3BV of 80% acetone. The detection results showed that Timosaponin BII was mainly collected in the fraction of 35% acetone. This fraction was concentrated to remove acetone and spray dried to obtain crude sample of Timosaponin BII (45.0 g). About 40 g of the crude sample was dissolved in 200 mL of 10% acetone, and chromatographed on a Sephadex LH-20 column (8.5 L), which was pre-equilibrated with 10% acetone. The column was eluted with 10% acetone (40.000 mL), and then regenerated with 80% acetone (20,000 mL). The eluate of 10% acetone was collected in fractions with 800 mL per fraction, and the purity of each fraction was detected by HPLC. She fractions 20 to 36 were combined and concentrated to remove acetone until a small volume and then lyophilized to obtain to give Timosaponin BII (9.2 g). The yield of the product was 0.52% of the root material, and the purity, as detected by HPLC, was 91.7%.

Example 6

Preparation of Timosaponin BII

The fresh rhizomes of *Anemarrhena asphodeloides* Bunge (4 kg) was sliced, to which 8 L of 50% ethanol % vas added. The drug was immersed for 2 hours and then extracted for 0.5 hour with an ultrasonic wave oscillator before filtering. The residue was similarly ultrasound extracted for more two times. The ethanol extracts were combined and concentrated under reduced pressure to remove ethanol until 10 L. A pretreated macroporous resin AB-8 (Tianjin Nankai Chemical Plant) was loaded on a column (6 L), which was equilibrated with water. The concentrated extract was filtered, and the filtrate was chromatographed on the column and eluted with water to remove the impurity. Thereafter, the column was eluted in sequence with 3BV of 20% ethanol, 3BV of 50% ethanol and 3BV of 95% ethanol. The detection results showed that Timosaponin BII was mainly collected in the fraction of 50% ethanol. This fraction was concentrated to remove ethanol until a small volume, and then dried in vacuo to obtain crude sample of Timosaponin BII (59.3 g). 50 g of the crude sample was dissolved in 200 mL of 25% acetone, and chromatographed on a silica gel RP-18 column (6.5 L), which was pre-equilibrated with 25% acetone. The column was eluted in sequence with 28% acetone (20,000 mL) and 30% acetone (20,000 mL), and then regenerated with 80% acetone (15,000 mL). The eluates with 28% acetone and 30% acetone were collected in fractions with 600 mL per fraction, and the purity of each fraction was detected by HPLC. The fractions 6 to 25 were combined and concentrated to remove acetone until a small volume and then lyophilized to obtain to obtain Timosaponin BII (15.6 g). 14.1 g of the sample was dissolved in 70 mL of 25% acetone solution, and chromatographed on a silica gel RP-18 column (6.5 L), which was pre-equilibrated with 25% acetone. The column was eluted with 28% acetone (40,000 mL), and then regenerated with 80% acetone (1,200 mL). The eluate was collected in fractions with 600 mL per fraction, and the purity of each fraction was detected by HPLC. The fractions 8 to 19 were combined and concentrated to remove acetone until a small volume and then lyophilized to obtain Timosaponin BII (4.5 g). The yield of the product was 0.15% of the fresh rhizomes (corresponding to the yield of 0.44% on the basis of the dry medicinal material), and the purity, as detected by HPLC, was 98.6%.

The product was a white amorphous powder, with mp>243° C. (dec), and being positive for both Liebermann-Burchard reaction and Molish reaction, and also positive for Ehrlich reagent.

The structure of obtained Timosaponin BII was identified, by means of IR, MS and NMR, as follows:

IR (diffuse reflection) $cm^{-1}$: 3348 (OH), 2930, 2850, 1075, 1044 (glycoside linkage C—O).

FAB-MS (m/z): 943$(M+Na)^+$, 903$(M+H-H_2O)^+$, 741 $(M+H_2O-Glc)^+$, 579$(M+H-H_2O-Glc\times 2)^+$, 417$(M+H-H_2O-Glc\times 2-Gal)^+$, 399$(aglycon+H-H_2O\times 2)^+$, 255, 185, 145.

EI-MS (m/z): 740$(M-H_2O-Glc)^+$, 578$(M-H_2O-Glc\times 2)^+$, 416 $(aglycon-H_2O)^+$, 415$(aglycon-H-H_2O)^+$, 357, 273, 217, 181, 139.

$^1$H-NMR ($C_5D_5N$) δ: 0.85 (3H, S, 18-$CH_3$), 0.96 (3H, S, 19-$CH_3$), 1.00 (3H, d, J=6.4 Hz, 27-$CH_3$), 1.30 (3H, d, J=6.8 Hz, 21-$CH_3$), 4.79 (1H, d, J=7.8 Hz, Glc 1-H), 4.90 (1H, d, J=7.8 Hz, Gal 1-H), 5.27 (1H, d, J=7.8 Hz, Glc 1-H).

$^{13}$C-NMR data is shown in Table 1. The compound was (25S)-26-O-β-D-glucopyranosyl-22-hydroxy-5β-furostane-3β, 26-diol-3-O-D-glucopyranosyl-(1→2)-β-D-galactopyranoside.

TABLE 1

$^{13}$C-NMR chemical shifts of Timosaponin BII (δ in pyridine-$d_5$)

| position (aglycon) | δc | position (glycosyl) | δc |
|---|---|---|---|
| 1 | 30.9 | gal-1 | 102.5 |
| 2 | 27.0 | 2 | 81.8 |
| 3 | 75.0 | 3 | 76.9 |
| 4 | 30.9 | 4 | 69.8 |
| 5 | 36.9 | 5 | 76.5 |
| 6 | 26.7 | 6 | 62.1 |
| 7 | 26.7 | glc-1 | 106.1 |
| 8 | 35.4 | 2 | 75.5 |
| 9 | 40.2 | 3 | 78.0 |
| 10 | 35.2 | 4 | 71.4 |
| 11 | 21.1 | 5 | 78.4 |
| 12 | 40.4 | 6 | 62.7 |
| 13 | 41.2 | 26glc-1 | 105.1 |
| 14 | 56.4 | 2 | 75.2 |
| 15 | 32.4 | 3 | 78.5 |
| 16 | 81.2 | 4 | 71.6 |

TABLE 1-continued $^{13}$C-NMR chemical shifts of Timosaponin BII ($\delta$ in pyridine-d$_5$)

| position (aglycon) | $\delta$c | position (glycosyl) | $\delta$c |
|---|---|---|---|
| 17 | 64.0 | 5 | 78.4 |
| 18 | 16.7 | 6 | 62.7 |
| 19 | 24.0 | | |
| 20 | 40.6 | | |
| 21 | 16.4 | | |
| 22 | 110.6 | | |
| 23 | 37.1 | | |
| 24 | 28.3 | | |
| 25 | 34.4 | | |
| 26 | 75.3 | | |
| 27 | 17.4 | | |

Comparative Example 1

Preparation of Timosaponin BII

The decoction pieces of Chinese traditional medicine Rhizoma Anemarrhenae (1 kg) were ground, to which 6 L of 60% ethanol was added. The drug was immersed for one hour and then reflux extracted by heating for one hour before filtering. The residue was similarly reflux extracted for more two times. The ethanol extracts were combined and concentrated to remove ethanol under reduced pressure until 4 L. 4 L of n-butanol saturated with water was added to the concentrated solution. The obtained solution was homogeneously mixed by shaking, and stratified after standing for a while. Then, the n-butanol layer was collected, and the aqueous layer was similarly extracted for more 4 times by adding n-butanol saturated with water. The five-time n-butanol extracts were combined and concentrated to dryness thereby obtaining saponins (33.1 g). The saponins was dissolved in methanol, and mixed with silica gel (60 g), and then heated to evaporate the solvent to dryness. The mixed sample was chromatographed on a silica gel column (3 L) that was packed by a dry method, and eluted with a gradient mixture of chloroform-methanol-water. The chloroform-methanol-water (60:40:10, lower phase) eluate containing Timosaponin BII was collected and concentrated to dryness thereby obtaining crude product (2.3 g). The crude product was further chromatographed on a silica gel column (500 mL), and eluted with chloroform-methanol-water. The eluate of chloroform-methanol-water (65:35:10, lower phase) was collected in fractions with 50 mL per fraction. The fractions 15 to 23 were concentrated to dryness thereby obtaining product (0.67 g). The product was dissolved in 32% methanol, and chromatographed on a silica gel RP-18 column (600 mL). The column was eluted in sequence with 32% methanol (1,800 mL) and 34% methanol (1,800 mL), and then regenerated with 90% methanol (1,200 mL). The eluates of 32% methanol and 34% methanol were collected in fractions with 50 mL per fraction, and the purity of each fraction was detected by HPLC. The fractions 13 to 21 were combined and concentrated to remove methanol until a small volume and then lyophilized to obtain Timosaponin BII (0.34 g). The purity, as detected by HPLC, was 75.5%. The product was dissolved in 30% acetone, refluxed in a water bath at 95° C. for 5 hours, and concentrated to remove acetone and then lyophilized to obtain Timosaponin BII (0.33 g). The yield of the product was 0.033% of the raw medicinal material, and the purity was 93.4%.

The invention claimed is:

1. An improved method for preparing Timosaponin BII, the method comprising:
   a) providing the decoction pieces of Chinese traditional medicine Rhizoma Anemarrhenae or fresh rhizome or fibrous root of *Anemarrhena asphodeloides* Bunge as raw material and extracting with a solvent selected from the group consisting of water, acetone, ethanol, and the mixture of at least two of them;
   b) separating the extract solution obtained from a) by one or more methods selected from the group consisting of resin adsorption, polyamide chromatography and reversed-phase column chromatography, and eluting by an eluant selected from the group consisting of water, acetone, ethanol and a mixture of at least two of them;
   c) combining the eluates of b), drying and obtaining Timosaponin BII; wherein
   the method for preparing Timosaponin BII does not use n-butanol, methanol or normal phase silica gel column chromatography.

2. The method of claim 1 wherein the extraction in a) is extraction at room temperature or with heating, or ultrasonic extraction, and the extraction is performed one or more times.

3. The method of claim 1 wherein the solvent extraction in a) is extraction by a method selected from the group consisting of:
   reflux, percolation or ultrasonic extraction with 10 to 95% ethanol in water; and
   reflux, percolation or ultrasonic extraction with 10 to 80% acetone in water, after decocting the raw material in water.

4. The method of claim 1 wherein in the resin absorption in b), the resin used is a macroporous resin of the polystyrene type, the eluent used is selected from the group consisting of water, acetone, and ethanol, and the elution may be isocratic elution or gradient elution.

5. The method of claim 4 wherein the resin in b) is adsorption resin of the D-101 type, adsorption resin of the AB-8 type, adsorption resin of the XAD-2 type, adsorption resin of the HP20 type, adsorption resin of the SP825 type, adsorption resin of the SP700 type, adsorption resin of the CHP-20P type or adsorption resin of the SP70 type.

6. The method of claim 5 wherein the resin adsorptive process comprises adsorbing the extract solution on macroporous resin, removing the impurity by eluting with water or 5 to 30% acetone, or ethanol in water in an amount of 2 to 7 times column volume, and then eluted with 20 to 70% acetone or ethanol in water in an amount of 2 to 7 times column volume.

7. The method of preparing Timosaponin BII of claim 1 wherein the polyamide chromatography in b) is column chromatography or static adsorption filtration method, and the eluent is a solvent selected from the group consisting of water, acetone and ethanol and the elution may be isocratic elution or gradient elution.

8. The method of claim 1 wherein the polyamide chromatography in b) comprises loading the aqueous solution of Timosaponin BII on a polyamide column, and then eluting it with water or 0 to 15% acetone or ethanol solution in water in an amount of 2 to 5 times column volume.

9. The method of claim 1 wherein the reversed-phase column chromatography is a normal pressure or pressurized reversed-phase column chromatography, the column stuffing is silica gel RP-18 (ODS) or RP-8, the eluent is selected from the group consisting of acetone-water and ethanol-water, and the elution may be isocratic elution or gradient elution.

10. The method of preparing Timosaponin BII of claim 1, wherein the eluent is selected from the group consisting of acetone-water, ethanol-water and a mixture thereof.

* * * * *